(12) United States Patent
Whang

(10) Patent No.: US 10,154,669 B2
(45) Date of Patent: Dec. 18, 2018

(54) IMPROVING COLOR AND RELEASE PROFILE OF RESIN COMPOSITIONS COMPRISING SILVER NANOPARTICLES

(71) Applicant: The Board of Regents of the University of Texas System, Austin, TX (US)

(72) Inventor: Kyumin Whang, Helotes, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 129 days.

(21) Appl. No.: 15/026,971

(22) PCT Filed: Oct. 2, 2014

(86) PCT No.: PCT/US2014/058929
§ 371 (c)(1),
(2) Date: Apr. 2, 2016

(87) PCT Pub. No.: WO2015/051196
PCT Pub. Date: Apr. 9, 2015

(65) Prior Publication Data
US 2016/0255840 A1    Sep. 8, 2016

Related U.S. Application Data

(60) Provisional application No. 61/885,644, filed on Oct. 2, 2013.

(51) Int. Cl.
*A01N 59/16* (2006.01)
*A61K 6/00* (2006.01)
*A61K 6/083* (2006.01)
*C09D 5/14* (2006.01)

(52) U.S. Cl.
CPC ............. *A01N 59/16* (2013.01); *A61K 6/007* (2013.01); *A61K 6/083* (2013.01); *C09D 5/14* (2013.01)

(58) Field of Classification Search
None
See application file for complete search history.

(56) References Cited

U.S. PATENT DOCUMENTS

| | | | | |
|---|---|---|---|---|
| 2,833,753 | A * | 5/1958 | Lal | C08F 4/00 502/167 |
| 3,672,942 | A * | 6/1972 | Neumann et al. | B22D 31/005 427/295 |
| 5,760,100 | A * | 6/1998 | Nicolson | G02C 7/049 351/159.33 |
| 6,267,590 | B1 * | 7/2001 | Barry | A61C 7/14 433/20 |
| 6,716,895 | B1 * | 4/2004 | Terry | A61L 27/34 523/122 |
| 6,759,431 | B2 * | 7/2004 | Hunter | A61K 9/0024 424/403 |

(Continued)

*Primary Examiner* — Peter A Salamon
(74) *Attorney, Agent, or Firm* — Winstead PC

(57) ABSTRACT

Methods of forming antimicrobial resin compositions comprising silver nanoparticles are disclosed. Such methods generally comprise: combining a silver-containing material with a resin in situ in the presence of a silver-binding compound; and curing the resin. Antimicrobial polymeric resin compositions formed by said methods have a lighter color than control compositions and also display a slower release of silver ions over time.

8 Claims, 3 Drawing Sheets

(56) References Cited

U.S. PATENT DOCUMENTS

| | | |
|---|---|---|
| 2005/0013842 A1* | 1/2005 | Qiu ................. A61L 12/088 |
| | | 424/423 |
| 2005/0203237 A1* | 9/2005 | Cornelius Maria Dekkers .......... |
| | | A01N 59/16 |
| | | 524/450 |
| 2006/0246149 A1 | 11/2006 | Buchholz et al. |
| 2007/0009448 A1 | 1/2007 | Kanca |
| 2007/0231295 A1* | 10/2007 | Hoppe ................. A61K 8/25 |
| | | 424/78.09 |
| 2008/0085494 A1 | 4/2008 | Mader et al. |
| 2008/0181931 A1* | 7/2008 | Qiu ................. A61L 12/088 |
| | | 424/429 |
| 2009/0074705 A1* | 3/2009 | Graham ............ A01N 59/16 |
| | | 424/78.17 |
| 2011/0306699 A1* | 12/2011 | Whang ............. A01N 59/16 |
| | | 523/113 |

* cited by examiner

IMPROVING COLOR AND RELEASE PROFILE OF RESIN COMPOSITIONS COMPRISING SILVER NANOPARTICLES

CROSS-REFERENCES TO RELATED APPLICATIONS

This Application claims the benefit under 35 U.S.C. § 119(e) of U.S. Provisional Patent Application No. 61/885,644 filed Oct. 2, 2013, which is incorporated herein by reference in its entirety as if fully set forth herein. This Application incorporates by reference, the entirety of U.S. patent application Ser. No. 13/162,454 filed Jun. 16, 2011.

TECHNICAL FIELD

This invention relates to a resin composition comprising silver particles that exhibits improved color and release profile of the silver ions.

BACKGROUND OF THE INVENTION

Resin based restorative materials are the material of choice by doctors and patients due to their good mechanical properties, biocompatibility and aesthetic properties. A resin-based composition that possesses antimicrobial properties and inhibits microbial growth would be desirable. The applications that such an antimicrobial resin could be useful in include, products that can be used in medical applications including orthopedic applications and dental applications such as dental cements, luting agents and restorative materials. Various antibacterial agents have been incorporated into dental products such as rinse solutions, toothpastes, coatings, and dental resins to kill bacteria or inhibit bacterial growth, as well as in medical and other commercial products. Silver has been shown to be an effective antibacterial agent. However silver-based compositions often tend to be colored ("yellow" to "amber") and then "darken" or "blacken" upon storage and degrade the aesthetic appearance of these compositions rendering the material inapplicable to many products. Therefore, it would be desirable to create a silver-based resin composition that displays the antimicrobial properties of silver without the associated coloring and/or darkening or blackening.

SUMMARY OF THE INVENTION

An embodiment of the invention is directed to methods of making silver nanoparticle containing resin compositions having a lower initial color (less yellow, more white) and reduced color shift, i.e., change in color over time. An embodiment of the invention provides a method of making an antimicrobial resin composition containing silver nanoparticles, by selecting a silver-containing material, an acrylic resin monomer and a solvent that is miscible with the silver-containing material and with the acrylic resin monomer; combining the acrylic resin monomer with a silver binding compound, combining the silver-containing material with the solvent to form a silver-containing material solution; mixing the silver-containing material solution with the mixture of the acrylic resin monomer and silver binding compound in situ to form an acrylic resin monomer solution; forming silver nanoparticles within the acrylic resin monomer solution by curing the acrylic resin monomer solution, wherein the curing process converts the acrylic resin monomer to a polymer; and forming an antimicrobial, resin composition. Other embodiments of the present disclosure provide antimicrobial resin compositions produced by the foregoing methods.

The foregoing has outlined rather broadly the features of the present disclosure in order that the detailed description that follows may be better understood. Additional features and advantages of the disclosure will be described hereinafter, which form the subject of the claims.

DETAILED DESCRIPTION OF EXEMPLARY EMBODIMENTS

Figure 1:
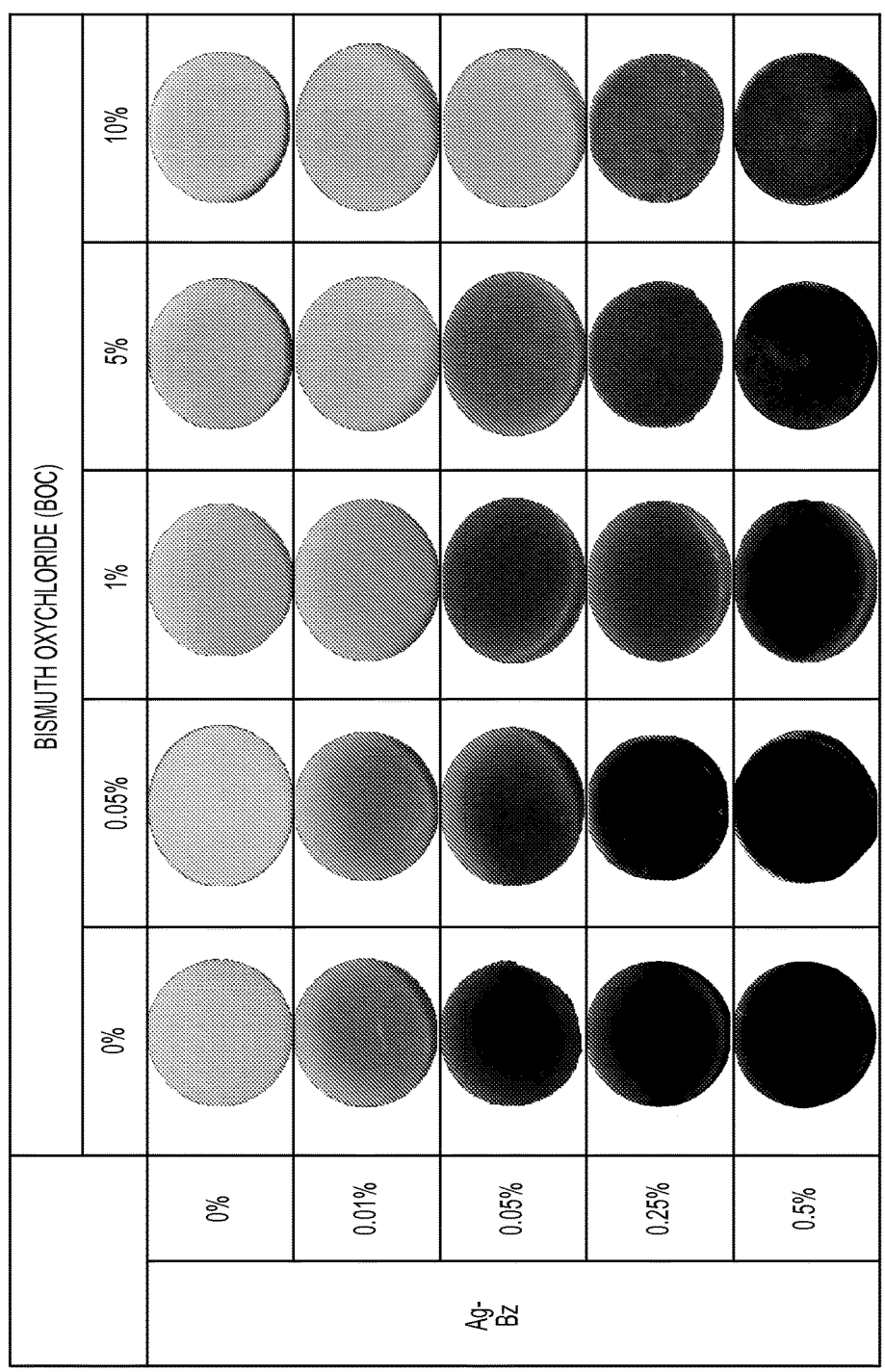
FIG. 1 shows the effect of adding silver and bismuth OxyChloride (BOC) on the color of resins.

In the following description, certain details are set forth so as to provide a thorough understanding of the present embodiments disclosed herein. However, it will be understood by those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

The definitions and explanations as set forth herein are meant and intended to be controlling in any future construction unless clearly and unambiguously modified in the following Description or when application of the meaning renders any construction meaningless or essentially meaningless. In cases where the construction of the term would render it meaningless or essentially meaningless, the definition should be taken from Webster's Dictionary, 3rd Edition. Definitions and/or interpretations should not be incorporated from other patent applications, patents, or publications, related or not, unless specifically stated in this specification or if the incorporation is necessary for maintaining validity.

Other than in the operating examples, or where otherwise indicated, all numbers expressing quantities of components used herein are to be understood as modified in all instances by the term "about".

The present disclosure pertains to methods of forming antimicrobial resin compositions that comprise in situ generated silver nanoparticles. In some embodiments, the invention provides a method of making an antimicrobial resin composition containing silver nanoparticles, by selecting a silver-containing material, an acrylic resin monomer and a solvent that is miscible with the silver-containing material and with the acrylic resin monomer; combining the acrylic resin monomer with a silver binding compound, combining the silver-containing material with the solvent to form a silver-containing material solution; mixing the silver-containing material solution with the mixture of the acrylic resin monomer and silver binding compound in situ to form an acrylic resin monomer solution; forming silver nanoparticles within the acrylic resin monomer solution by curing the acrylic resin monomer solution, wherein the curing process converts the acrylic resin monomer to a polymer; and forming an antimicrobial, resin composition. Other embodiments of the present disclosure provide antimicrobial resin compositions produced by the claimed methods.

As used herein, the term, "antimicrobial" means that the article exhibits one or more of the following properties: the inhibition of the adhesion of bacteria or other microbes to the article; the inhibition of the growth of bacteria or other microbes on the article; and/or the killing of bacteria or other microbes on the surface of the article or in an area surrounding the article. For purposes of this invention, adhesion of bacteria or other microbes to the article, the growth of bacteria or other microbes on the article and the presence of bacterial or other microbes on the surface of the article are collectively referred to as "microbial colonization." In various embodiments, the articles of the present disclosure exhibit varying levels of inhibition of viable bacteria or other microbes. Such bacteria or other microbes include but are not limited to Pseudomonas aeruginosa, Acanthamoeba species, Staphyloccus aureus, Escherichia coli, Staphyloccus epidermidis, Serratia marcesens, Acinetobacter baumannii and/or the like.

As used herein, the term "patient" means and refers to a human or animal. Suitable examples include, but are not limited to a human or an animal (e.g., a dog, a cat, a horse, a bird, a reptile, an amphibian, a fish, a turtle, a guinea pig, a hamster, a rodent, a cow, a pig, a goat, a primate, a monkey, a chicken, a turkey, a buffalo, an ostrich, a sheep, a llama).

As used herein, the term "chemically feasible" refers to a connectivity of atoms such that the chemical valency of each atom is satisfied. For example, an oxygen atom with two bonds and a carbon atom with four bonds are chemically feasible.

As used herein, the term "nanoparticle(s)" means and refers to small particles ranging from small visible particles to particles on the nano-scale. As used herein, the term "metallic nanoparticle(s)" means and refers to nanoparticles that contain one or more metals, such as silver.

As used herein, the term "polymeric" means and refers to a composition(s) that comprises one or more monomers, oligomers, polymers, copolymers, or blends thereof. Suitable examples of polymers include, but are not limited to, polyvinyl alcohol, poly ethylene glycol, ethyl cellulose, polyolefins, polyesters, nonpeptide polyamines, polyamides, polycarbonates, polyalkenes, polyvinyl ethers, polyglycolides, cellulose ethers, polyvinyl halides, polyhydroxylkanoates, polyanhydrides, polystyrenes, polyacrylates, polymethacrylates, polyurethanes, polypropylene, polybutylene terephthalate, polyethylene terephthalate, nylon 6, nylon 6,6, nylon 4,6, nylon 12, phenolic resins, urea resins, epoxy resins, silicone polymers, polycarbonates, polyethylene vinylacetate, polyethylene ethyl acrylate, polylactic acid, polysaccharides, polytetrafluoroethylene, polyvinylidenes, polyphosphazines, chlorinated polyethylenes, polysulfones and copolymers and blends thereof. Applicants also note that the terms "polymeric", "polymer" and "resin" may be used interchangeably in the present disclosure.

As used herein, the term "water soluble" or use of the term "miscible in water" means and refers to a level of solubility such that when a composition is placed in water, greater than about 2.0 percent by weight of the composition dissolves. For example, methyl methacrylate (MMA) is considered substantially non water soluble, yet has a water solubility of about 1.6 g in 100 g of water.

As used herein, the term "%" is intended to refer to % by weight or wt %, unless otherwise indicated.

Currently, polymeric materials, such as polymethyl methacrylate (PMMA), are used in many industries for numerous purposes. For instance, polymeric resin materials are used in dentistry, orthopedics and craniofacial surgery. However one major problem with the utilization of polymeric resin materials is the occurrence of infections (e.g., caries in dentistry). For example, but not by way of limitation, approximately 10% of soldiers returning from various battlefields develop infections after receiving craniofacial implants. Likewise, failure of orthopedic implants is often due to the periprosthetic infections of the PMMA bone cement. Current therapies to treat the more severe cases of infections involve the use of local and systemic antibiotics. However, antibiotic therapy poses the problem of generating resistant strains of bacteria. In the military, this is of special concern because many troops returning from various battlefields are infected with Acinetobacter baumannii, a multi-antibiotic resistant bacteria. Resin compositions of the claimed invention are also applicable in dental applications such as dental cements, luting agents and restorative materials. Furthermore, resin compositions of the claimed invention can be used in non-medical commercial applications as well.

Accordingly, antimicrobial agents have been added to many polymeric materials in order to prevent infections during their various uses. For instance, silver salts have been used in human healthcare and medicine as an antiseptic for post surgical infections. Silver salts have also been used as an anti-microbial agent for various purposes in dental devices, wound therapy, medical devices, and/or the like. Specifically, silver nitrate has been used to prevent ophthalmic neonatorum in newborns.

However, as discussed previously, silver particle-containing polymers tend to have a "yellow" to "amber" color at low concentrations and/or tend to darken or blacken during storage and thus, tend to lose their aesthetic appeal. Accordingly, the claimed invention provides novel methods of forming antimicrobial polymeric materials and novel resulting products and compositions of matter that have improved color profile relative to existing silver containing resin compositions and also exhibit a more gradual release of silver from the resin. In some embodiments, the present disclosure provides methods of forming an antimicrobial resin composition that comprises a silver nanoparticle. Such methods generally comprise: (1) combining a silver-containing material with a resin in situ, wherein the resin monomer is first combined with a silver-binding compound; and (2) curing the resin mixture in the presence of the silver-containing material.

As explained below, numerous metal containing materials and resins may be used in various embodiments of the present disclosure. Likewise, various curing methods may be used to form the polymeric materials of the present disclosure.

Metal Containing Materials

A person of ordinary skill in the art will recognize that various silver containing materials may be used with the methods and compositions of the present disclosure. Specific examples include silver-containing materials (e.g., silver, silver alloys, silver oxides, silver carbides, silver nitrides, silver borides, silver borate, silver sulfides, silver myristates, silver stearates, silver oleates, silver gluconates, silver adipates, silver silicates, silver phosphides, silver halides, silver hydrides, silver nitrates, silver carbonates, silver sulfadiazines, silver acetates, silver lactates, silver citrates, alkali silver thiosulphates (e.g., sodium silver thio sulphate, potassium silver thio sulphate)).

In some embodiments, the silver containing materials are soluble in organic solvents and acrylic monomers. In more specific embodiments, metal containing materials may be silver oleates, silver gluconates, silver adipates, silver sulfadiazines, silver acetates, silver benzoate and the like. In further embodiments, the metal containing material is silver benzoate.

Resins

A person of ordinary skill in the art will also recognize that various resins may be used with the methods and compositions of the present disclosure. Non-limiting examples include acrylic resins. Acrylic resins include, but are not limited to, any resin containing an acrylate group (=CR—COOR'), where R and R' can be hydrogen, methyl, ethyl, butyl, benzoyl, or any alkyl or aryl group that is chemically feasible.

Other examples of resins that may be used with various embodiments of the present disclosure includes poly (methyl methacrylate) (PMMA) resins (an oil-based acrylic resin), other oil-based resins, water soluble resins, and/or the like.

More specific examples of resins that can be used with various embodiments of the present disclosure include, without limitation: Bis-GMA (bisphenol glycidyl methacrylate) based resins; TEGDMA (triethylene glycol dimethacrylate) based resins; HEMA (2-hydroxyethyl methacrylate) based resins; PMDM (pryomellitic acid diethylmethacrylate) based resins; PMGDM (pyromellitic acid glycerol dimethacrylate) based resins; UDMA (urethane dimethacrylate) based resins; methacrylate based resins; dimethacrylate based resins; hydrophobic resins; hydrophilic resins; and hardenable monomers suitable for dental and orthopedic applications.

Generally, oil-based resins are not soluble in water or have limited solubility in water such that less than about 2.0% by weight of the resin dissolves when placed in water. There are many types of oil-based resins that are suitable for the present disclosure. Specific examples of acrylic resins include, but are not limited to:

Poly(acrylonitrile-co-vinylidene chloride-co-methyl methacrylate):

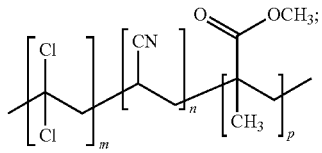

Poly(benzyl methacrylate):

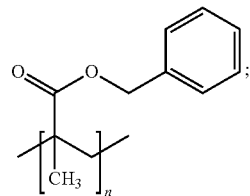

Poly(butyl methacrylate):

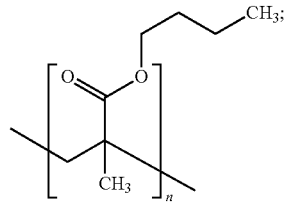

Poly(tert-butyl methacrylate):

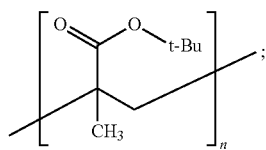

Poly(butyl methacrylate-co-isobutyl methacrylate):

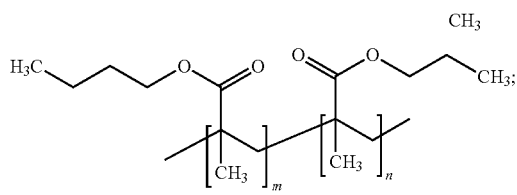

Poly(butyl methacrylate-co-methyl methacrylate):

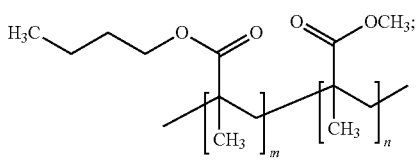

Poly(cyclohexyl methacrylate):

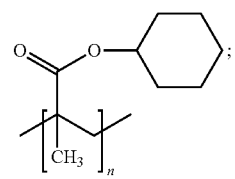

Poly[(2-ethyldimethylammonioethyl methacrylate ethyl sulfate)-co-(1-vinylpyrrolidone)]:

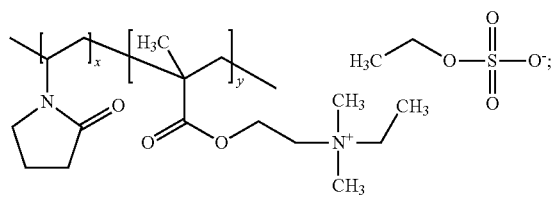

Poly(ethylene-co-glycidyl methacrylate):

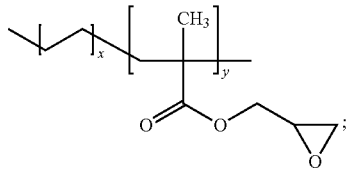

Poly(lauryl methacrylate-co-ethylene glycol dimethacrylate):

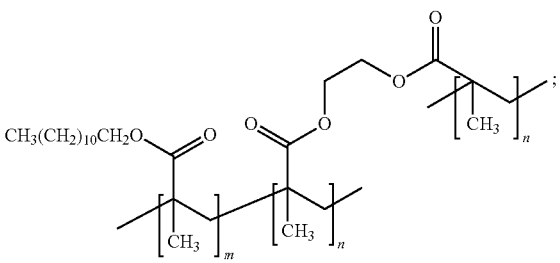

Poly(octadecyl methacrylate):

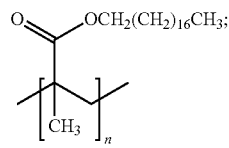

and
Poly(1-vinylpyrrolidone-co-2-dimethylaminoethyl methacrylate):

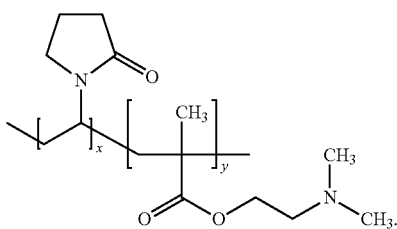

Curing

A person of ordinary skill in the art will also recognize that various methods may be used to cure resins in the present disclosure. Desirably, the curing occurs in situ in the presence of one or more metal containing materials in order to form polymeric materials with metallic nanoparticles.

In some embodiments, curing occurs by treating a resin with a chemical (i.e., chemical curing). In more specific embodiments, the resin is treated with one or more initiators, desirably in the presence of one or more metal containing materials. Non-limiting examples of suitable initiator systems include benzoyl peroxide (BPO) and dimethylparatoluidine (DMPT), and allyl thiourea (T) and cumene hydroperoxide (CH).

Initiators may be used at various concentrations and ratios for chemical curing. For instance, in some specific embodiments, chemical curing may consist of treating resins with allyl thiourea (T) and cumene hydroperoxide (CH). In other embodiments, chemical curing may consist of treating resins with benzoyl peroxide (BPO) and dimethylparatoluidine (DMPT).

In other embodiments, curing can occur by treating resins with a light source, such as ultraviolet and blue light (i.e., light curing). In other embodiments, curing may entail both light curing and chemical curing. Other methods of curing resins can also be envisioned by a person of ordinary skill in the art.

Applications

FIG. 1 shows the effect of adding silver and bismuth OxyChloride (BOC) on the color of resins. As the silver concentration increases so does color, but as BOC concentration increases the color decreases. This is clearly seen when the silver benzoate concentration is at 0.01% and at 0.05%. Increasing the concentration of BOC decreases the color of the resin.

Figure 2:
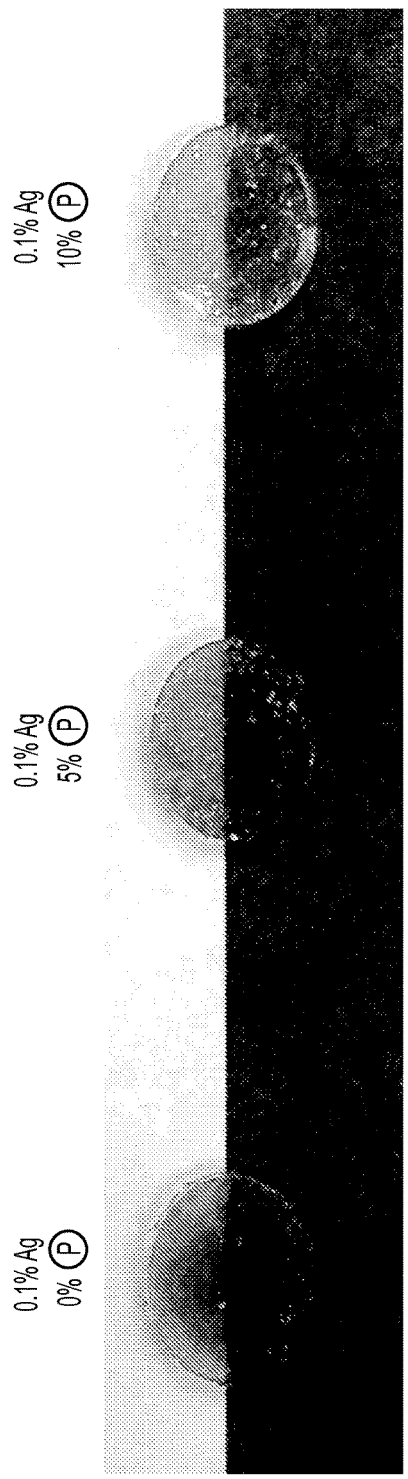
FIG. 2 shows the effect of adding a phosphate-containing monomer on the color of resins.

FIG. 2 shows the effect of adding a phosphate-containing monomer (P) on the color of resins. As the phosphate-containing monomer concentration increases, the color of the resin decreases. Increasing the concentration of phosphate-containing monomer from 5% to 10% causes a perceptible decrease in color of the resin.

Figure 3:
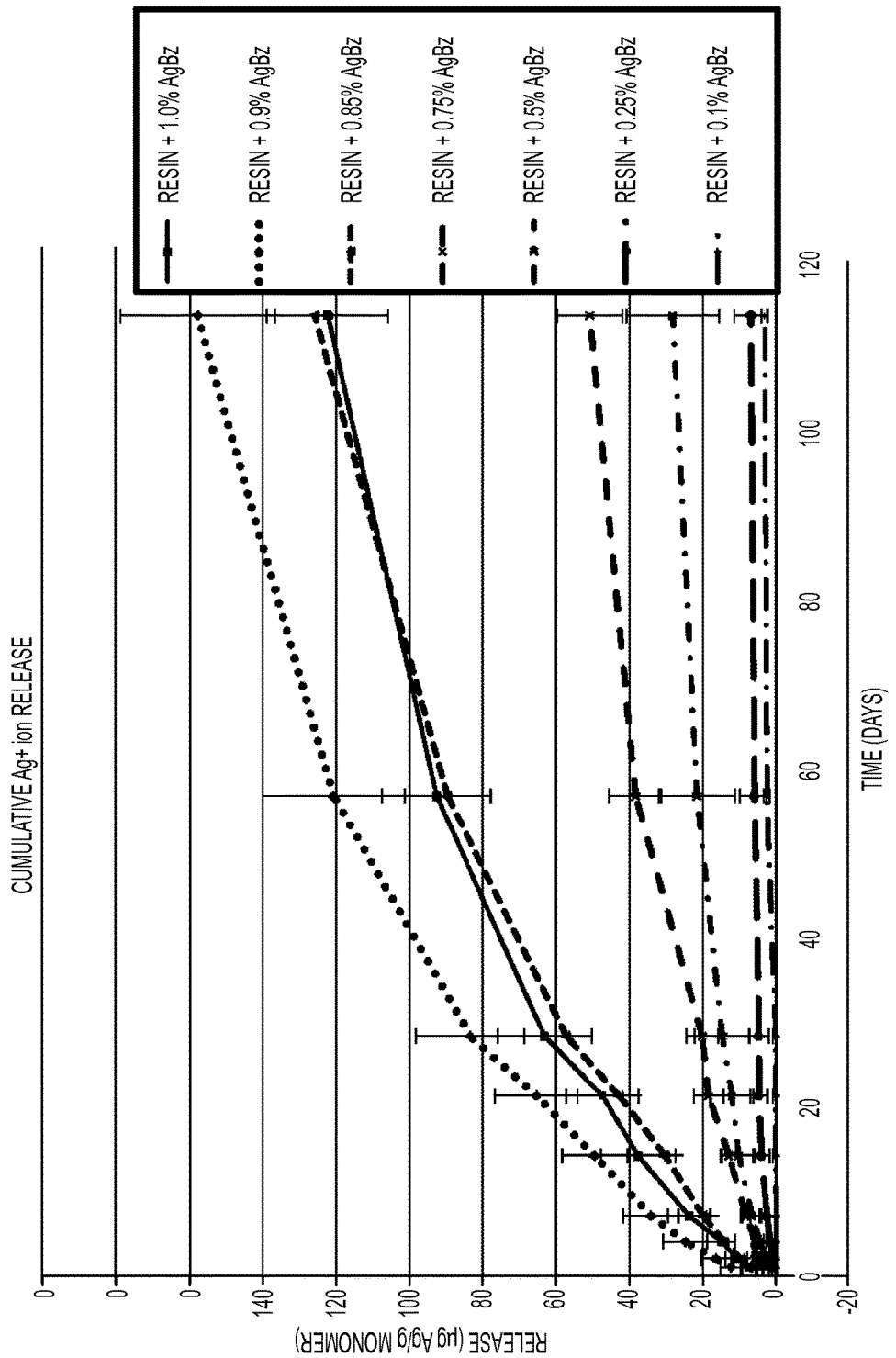
FIG. 3 shows a four (4) month release profile of silver from a silver-containing resin composition prepared in accordance with the claimed methods. It is noteworthy that the release profile is more gradual than compositions without the silver-binding compounds.

FIG. 3 shows a four (4) month release profile of silver from a silver-containing resin composition prepared in accordance with the claimed methods.

A person of ordinary skill in the art will recognize that the methods of the present disclosure can be used in various embodiments to form numerous anti-microbial resin compositions. For instance, in some embodiments, the methods of the present disclosure can be used to generate polymeric materials with silver nanoparticles (AgNP) by curing PMMA in the presence of a silver-binding compound and silver benzoate (AgBz).

An embodiment of the invention is directed to a method of making an antimicrobial resin composition containing silver nanoparticles, by selecting a silver-containing material, an acrylic resin monomer and a solvent that is miscible with the metal-containing material and with the acrylic resin monomer; combining the acrylic resin monomer with a silver binding compound; combining the silver-containing material with the solvent to form a silver-containing material solution; mixing the silver-containing material solution with the mixture of the acrylic resin monomer and the silver binding compound in situ to form an acrylic resin monomer solution; forming silver nanoparticles within the acrylic resin monomer solution by curing the acrylic resin monomer solution, wherein the curing process converts the acrylic resin monomer to a polymer; and forming an antimicrobial, resin composition.

In certain embodiments of the invention, the synthesized resin may be a dual cure resin or a self-cure resin that may be prepared using various combinations of resin monomers and suitable initiators. In various embodiments, herein disclosed are self-cure and dual-cure resins with silver nanoparticles that exhibit one or more of reduced color, reduced color shift, and/or reduced degree of self polymerization. In certain embodiments, compositions of the present invention comprise a camphorquinone (CQ) and 2-dimethylaminoethyl methacrylate (DMAEMA). In other embodiments of the invention, other photo initiators and co-initiators such as iodomium initiators may also be used.

In order to achieve a final resin composition that has a desirable color and exhibits a gradual release of silver, the resin monomer is mixed with a compound that is capable of binding silver ions present in the silver containing material. In an embodiment of the invention, the silver binding compound comprises an anionic group. In another embodiment of the claimed invention, the silver binding compound is bismuthoxychloride and/or a phosphate-containing acrylic resin. Following the mixing of the silver-binding compound with the resin monomer, the silver containing material is added to the resin mixture in order to generate silver particles in situ.

In addition to preventing the typical blackening or darkening color observed in silver containing resins, the addition of the silver binding compound to the resin monomer prior to the addition of the silver containing material, reduces the rate at which the silver is released from the resin. Both of these observations, i.e., the reduced darkening of the silver containing resin and the reduced rate of release of silver from the polymeric resin, are likely due to the fact that the chloride ions from the bismuthoxychloride and/or the phosphate ions from the phosphate-containing monomers bind the silver ions in the silver containing material (prior to polymer formation) and to the silver generated during the curing of the monomer.

From the foregoing detailed description of specific embodiments of the invention, it should be apparent that novel antimicrobial polymeric materials and novel methods of making such materials have been disclosed. Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. It is therefore contemplated that the claims will cover any such modifications or embodiments that fall within the true scope of the invention.

What is claimed is:

1. An antimicrobial resin composition comprising:
   an acrylic resin monomer;
   a silver-containing material dispersed in the acrylic resin monomer;
   a solvent that is miscible with the acrylic resin monomer and the silver-containing material; and
   a silver binding compound.

2. The antimicrobial resin composition of claim 1, wherein said acrylic resin is selected from the group consisting of bisphenol glycidyl methacrylate (Bis-GMA), poly (methyl methacrylate) (PMMA), triethylene glycol dimethacrylate (TEGDMA), 2-hydroxyethyl methacrylate (HEMA), pryomellitic acid diethylmethacrylate (PMDM), pyromellitic acid glycerol dimethacrylate (PMGDM), and urethane dimethacrylate (UDMA).

3. The antimicrobial resin composition of claim 1, wherein silver-containing material is selected from the group consisting of silver oleates, silver gluconates, silver adipates, silver sulfadiazines, silver benzoates and silver acetates.

4. The antimicrobial resin composition of claim 1, wherein said composition is used as a component of a medical device.

5. The antimicrobial resin composition of claim 4, wherein said medical device is a dental device.

6. The antimicrobial resin composition of claim 1, wherein the silver binding compound comprises an anionic group.

7. The antimicrobial resin composition of claim 1, wherein the silver binding compound comprises bismuth-oxychloride.

8. The antimicrobial resin composition of claim 1, wherein the silver binding compound comprises a phosphate-containing acrylic resin.

* * * * *